US00PP30986P2

(12) United States Plant Patent
Freyre et al.

(10) Patent No.: US PP30,986 P2
(45) Date of Patent: Oct. 29, 2019

(54) ***RUELLIA* PLANT NAMED 'R13-5-3'**

(50) Latin Name: *Ruellia simplex*
Varietal Denomination: R13-5-3

(71) Applicant: Florida Foundation Seed Producers, Inc., Marianna, FL (US)

(72) Inventors: Rosanna Freyre, Gainesville, FL (US); Victor Zayas, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 15/932,770

(22) Filed: Apr. 23, 2018

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1
CPC ..... A01H 5/02; A01H 6/00
See application file for complete search history.

*Primary Examiner* — Keith O. Robinson
(74) *Attorney, Agent, or Firm* — Koenig IP Works, PLLC

(57) ABSTRACT

'R13-5-3' is a new *Ruellia simplex* plant distinguished by having excellent performance under partial sun and in containers, medium-sized purple-violet flowers with a violet corolla tube, average plant height at 54 cm, profuse branching, and no fruit production, as disclosed.

2 Drawing Sheets

ACKNOWLEDGMENT OF FEDERAL RESEARCH SUPPORT

This invention was made with government support under FLA-ENH-005388 awarded by the National Institute of Food and Agriculture, USDA. The government has certain rights in the invention.

Genus and species: *Ruellia simplex*.
Cultivar denomination: 'R13-5-3'.

CROSS-REFERENCE TO RELATED APPLICATION n/a

BACKGROUND OF THE NEW CULTIVAR

The invention relates to a new and distinct variety of *Ruellia simplex* plant named 'R13-5-3'. 'R13-5-3' is an $F_2$ seedling from a manual hybridization conducted on Mar. 12, 2012, at the Environmental Horticulture Research Greenhouses (EHRG), University of Florida (UF) in Gainesville, Fla., between female parent 'R9-106' (UF proprietary clone, not patented; diploid, white corolla with purple throat) x male parent 'Chi Chi' (commercial cultivar, not patented; diploid, red-purple flowers). Ploidy level determinations were done by flow cytometry at UF using wild *R. simplex* as a diploid (2n=2x=34) control and 'Purple Showers' (commercial cultivar, not patented) as a tetraploid control. 'R13-5-3' is monoploid (n=x=17), which indicates that its origin was likely by haploid parthogenesis in the maternal parent.

'R13-5-3' has been reproduced asexually for over 4 years through vegetative cuttings (stem tip cuttings) and has been shown to retain its distinctive characteristics through successive asexual propagations.

'R13-5-3' has not been made publicly available more than one year prior to the filing date of this application.

SUMMARY OF THE INVENTION

The following are the most outstanding and distinguishing characteristics of 'R13-5-3' when grown under normal horticultural practices in Florida.

1. Excellent performance under partial sun environments and in containers;
2. Medium-sized purple-violet flowers with a violet corolla tube;
3. Average plant height of 54 cm;
4. Profuse branching; and
5. No fruit production.

DESCRIPTION OF THE FIGURES

This new *Ruellia simplex* variety 'R13-5-3' is illustrated by the accompanying photographs which show the plant's form and foliage. The colors shown are as true as can be reasonably obtained by conventional photographic procedures. The photographs were taken from seven-week old plants grown at the EHRG, UF, Gainesville, Fla.

DETAILED BOTANICAL DESCRIPTION OF THE CULTIVAR

Figure 1:
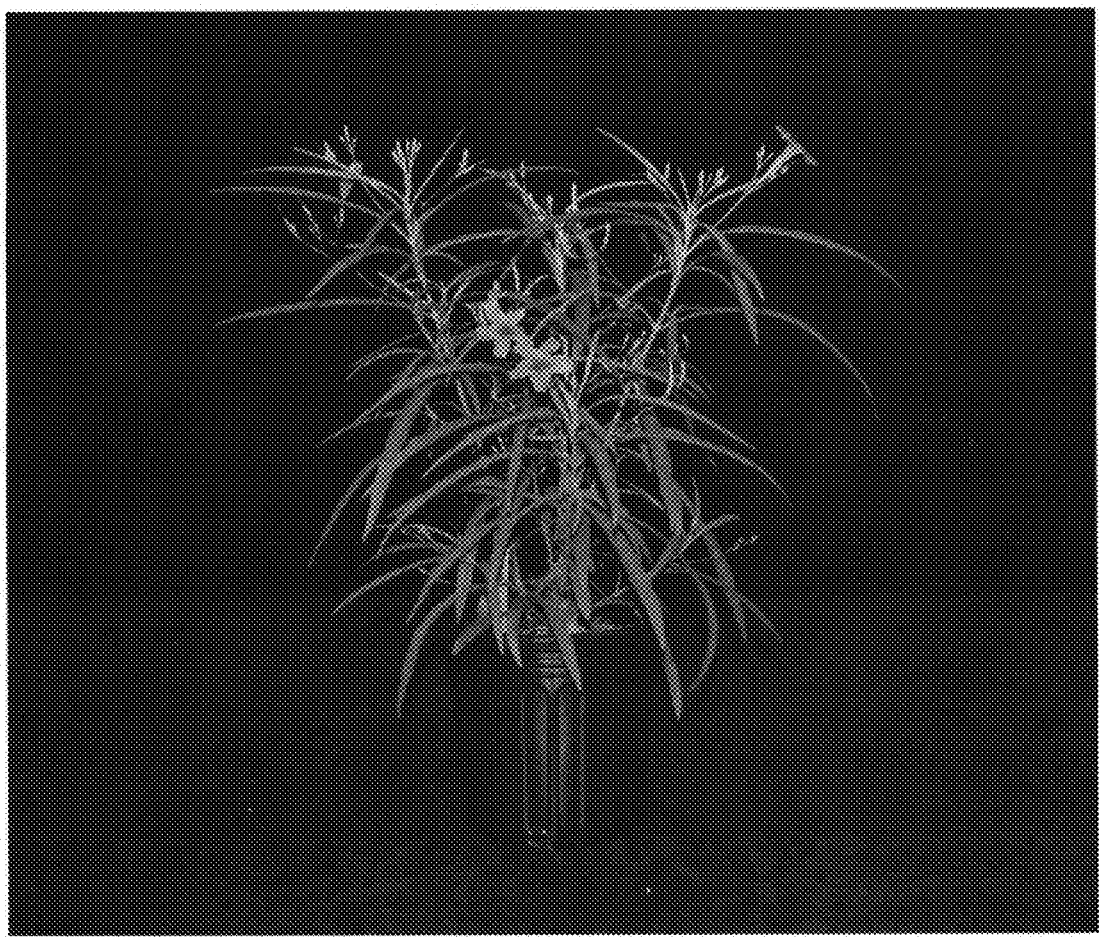
FIG. 1 shows a single plant of *Ruellia simplex* 'R13-5-3' in a one-gallon container, taken on Sep. 14, 2017, at the EHRG, UF, Gainesville, Fla.
Figure 2:
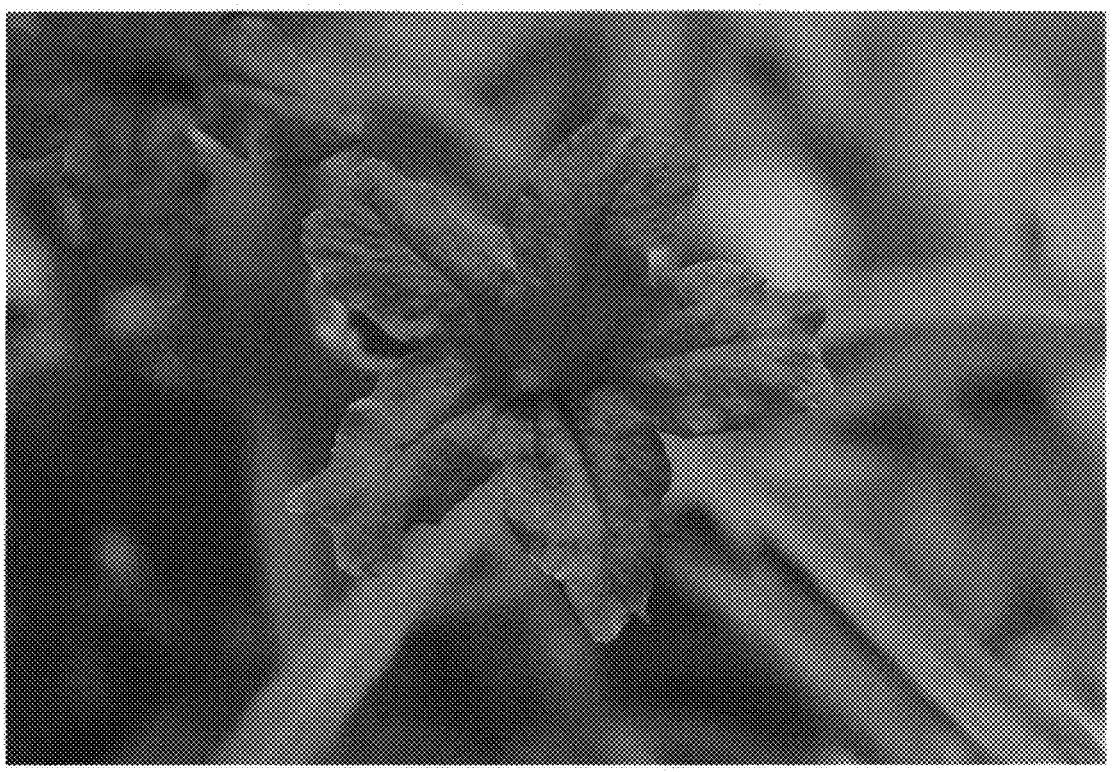
FIG. 2 shows a close-up view of a flower of *Ruellia simplex* 'R13-5-3' taken on Sep. 14, 2017, at the EHRG, UF, Gainesville, Fla.

The following detailed description sets forth the distinctive characteristics of 'R13-5-3'. Plants were propagated by vegetative cuttings on June 2016, and grown in the EHRG, UF, Gainesville, Fla. Plants were approximately seven weeks of age when the plant parts were measured and descriptions of color were determined. Color references are to The R.H.S. Colour Chart of The Royal Horticultural Society of London (R.H.S.), 2001 Edition.

BOTANICAL DESCRIPTION

Botanical classification:
*Family*.—Acanthaceae.

*Botanical name.*—*Ruellia simplex.*
*Common name.*—*Ruellia* (*Ruellia*) or Mexican petunia.
*Variety name.*—'R13-5-3'.

Plant description:
*Form.*—Erect.
*Habit.*—Clumping.
*Height* (*from top of soil*).—52-56 cm.
*Width* (*horizontal plant diameter*).—44-50 cm.

Propagation:
*Type.*—Vegetative meristems having at least two nodes.
*Time to initiate roots.*—7 days.
*Time to produce a rooted cutting.*—14 days.
*Root habit.*—Adventitious (fibrous).
*Root description.*—Callus forms in 4-5 days, roots initiate in 7 days and become a highly branched cutting in 14-21 days.

Branches:
*Quantity per plant.*—Approximately 30 when not pinched.
*Branch color.*—RHS 148A (yellow-green) with RHS 187B tint (greyed-purple) when mature. New growth is lighter in color (RHS 138B) and gets darker with light exposure.
*Texture.*—Smooth.
*Pubescence.*—Slightly tomentose, especially at nodes, RHS 155D (white).
*Stem description.*—Round to square shaped stem, 2.0-3.0 cm in diameter at the soil line.
*Branch diameter.*—1.0 cm at the base of a 45-cm-long branch.
*Branch length.*—45-50 cm.
*Internode length.*—2-5 cm.
*Anthocyanin.*—RHS 183B (greyed-purple).

Leaves:
*Quantity of leaves per branch.*—Approximately 50 on a 50-cm branch.
*Arrangement.*—Decussate (opposite pairs).
*Fragrance.*—None.
*Shape.*—Lanceolate.
*Length.*—8-15 cm.
*Width.*—0.8-1.2 cm.
*Apex.*—Narrowly acute.
*Base.*—Attenuate.
*Margin.*—Entire.
*Leaf texture* (*both surfaces*).—Slightly coriaceous.
*Venation color.*—Upper surface: RHS 138B (green). Lower surface: RHS 138C (green).
*Venation pattern.*—Pinnate.
*Color, mature and immature leaf.*—Upper surface: RHS 147A (green) immature, RHS 147A (green) mature. Lower surface: RHS 147B (green) immature, RHS 147A (green) mature.
*Petiole length.*—1-2 cm.
*Petiole diameter.*—0.2 cm.
*Petiole color.*—RHS 146B (yellow-green).

Flowers and seeds:
*Flower.*—Arrangement: Axillary in solitary or several-flowered cyme. Aspect: Actinomorphic corolla with five elongated petals, funnel form. Flowering habit (length of flowering season): April to October (north Florida). Number of inflorescences per plant: 4-8 cymes with 20-40 flowers plus buds. Fragrance: Very mild and slightly sweet. Lastingness of individual bloom: 1 day. Rate of opening: Daily.
*Flower bud.*—Shape: Elliptic. Length: 2.5 cm. Diameter: 0.5 cm. Color: RHS 150B (yellow-green), lower surface RHS 79C (purple). Texture: Smooth.
*Corolla.*—Arrangement: Actinomorphic salverform (funnel). Length: 3.0-3.5 cm. Diameter: 3.5-4.5 cm. Color: Upper surface: RHS 82B (purple-violet). Lower surface: RHS 82C (purple-violet). Texture: Rugose.
*Corolla tube.*—Length: 1.0 cm. Diameter: 0.5 cm. Color: RHS 83A (violet), includes bottom of lower petal.
*Banner.*—Not present.
*Keel.*—Not present.
*Calyx.*—Number of sepals per flower: 5. Length: 1.0 cm. Diameter: 0.3 cm. Apex: Narrowly acute. Base: Fused. Texture (both surfaces): Smooth to glandular. Pubescence: Present (glandular trichomes). Sepal color: Upper surface: RHS 143B (green). Lower surface: RHS 143B (green).
*Pedicels.*—Angle: 15-25°. Length: 1.0 cm. Diameter: 0.1 cm. Texture: Smooth to glandular (glandular trichomes). Color: Upper surface: RHS 79A (greyed-purple) under full sun, RHS 143B (green) in partial sun. Lower surface: RHS 143B (green).

Reproductive organs:
*Stamens.*—Number: 4 fused to the base of the corolla. Filaments: 4. Color: RHS 155D (white). Length: Two at 1.0 cm, two at 0.7 cm. Diameter: 0.1 cm. Anther color: RHS 155D (white). Pollen amount: Very sparse, most pollen grains are very small or deformed. Pollen color: RHS 155D (white).
*Pistils.*—Number per flower: 1. Pistil length: 2.2 cm. Stigma: Color: RHS 155D (white). Shape: Bilabial and slightly recurved. Length: 0.2 cm. Diameter: 0.2 cm. Style: Color: RHS 155D (white). Length: 2.0 cm. Diameter: 0.1 cm. Ovary: Shape: Hypogenous, elliptic. Color: RHS 143A (green). Length: 0.5 cm. Width: 0.1 cm.

Fruit/seed set: None observed.

Disease and insect resistance: Disease and insect resistance is typical of the species, thus no claims are made of any superior disease or insect resistance with this cultivar. The most common insect pests observed on this cultivar, particularly under greenhouse conditions in Gainesville, Fla., have been mealybugs (*Pseudococcidae*), spider mites (*Tetranychidae*), and aphids (*Aphidoidea*). No susceptibility to any particular pathogens has been observed on this cultivar.

COMPARISON WITH KNOWN CULTIVARS

When 'R13-5-3' is compared to the female parent 'R9-106', 'R13-5-3' has shorter plant height and purple-violet flowers with a violet corolla tube, while 'R9-106' has tall plant height and white corolla with violet corolla tube. When 'R13-5-3' is compared to the male parent 'Chi Chi', 'R13-5-3' has shorter plant height and purple-violet flowers with a violet corolla tube, while 'Chi-Chi' has tall plant height and red-purple flowers with darker red-purple corolla tube. 'R9-106' and 'Chi-Chi' form fruits and seeds while 'R13-5-3' does not.

When 'R13-5-3' is compared to UF variety 'R10-102' (U.S. Plant Pat. No. 24,422), the average plant height and plant width of 'R13-5-3' are 53.5 cm and 50.8 cm, respectively, which are significantly different to 'R10-102' with 70.9 cm and 64.0 cm, respectively. The average length of mature leaves of 'R13-5-3' is 13.0 cm, which is significantly longer than 'R10-102' with 8.3 cm, but average widths of mature leaves are similar at 1.0 cm and 1.2 cm, respectively. The average corolla diameter of 'R13-5-3' is 3.5-4.5 cm, which is significantly smaller than 'R10-102' with 5.4-6.7 cm. There is no fruit production on either 'R13-5-3' or 'R10-102'.

When 'R13-5-3' is compared to UF variety 'R12-2-1' (U.S. Plant Pat. No. 28,449), the average plant height and plant width of 'R13-5-3' are 53.5 cm and 50.8 cm, respectively, which is not significantly different to 'R12-2-1' with 62.8 cm and 55.5 cm, respectively. The average length of mature leaves of 'R13-5-3' is 13.0 cm, which is significantly longer than 'R12-2-1' with 8.5 cm. The average width of mature leaves for 'R13-5-3' is 1.0 cm, which is significantly narrower than 'R12-2-1' with 1.7 cm. The average corolla diameter of 'R13-5-3' is 3.5-4.5 cm, which is significantly smaller than 'R12-2-1' with 5.0-6.5 cm. There is no fruit production on either 'R13-5-3' or 'R12-2-1'.

We claim:

1. A new and distinct variety of *Ruellia* plant named 'R13-5-3' as illustrated and described herein.

* * * * *